United States Patent
Bowles et al.

[11] Patent Number: 6,113,538
[45] Date of Patent: Sep. 5, 2000

[54] ALERTNESS TESTER

[75] Inventors: Henry M. Bowles, Alameda; Theodore D. Langley, San Francisco, both of Calif.

[73] Assignee: Bowles-Langley Technology, Inc., Alameda, Calif.

[21] Appl. No.: 09/053,111

[22] Filed: Apr. 1, 1998

Related U.S. Application Data

[60] Provisional application No. 60/042,577, Apr. 2, 1997.

[51] Int. Cl.$^7$ .......................................................... A61B 5/00
[52] U.S. Cl. ........................................... 600/300; 600/558
[58] Field of Search ..................................... 600/300, 558; 180/272; 128/745; 364/413.02, 300

[56] References Cited

U.S. PATENT DOCUMENTS

| | | |
|---|---|---|
| 3,918,176 | 11/1975 | Abernethy, III et al. . |
| 4,004,290 | 1/1977 | Kobayashi et al. . |
| 4,006,539 | 2/1977 | Slomski . |
| 4,041,617 | 8/1977 | Hollander . |
| 4,058,113 | 11/1977 | Fields . |
| 4,058,911 | 11/1977 | Story . |
| 4,240,071 | 12/1980 | Ochiai . |
| 4,464,121 | 8/1984 | Perelli . |
| 4,723,625 | 2/1988 | Komlos ................................... 180/272 |
| 4,755,140 | 7/1988 | Rimland . |
| 4,770,636 | 9/1988 | Buschke . |
| 4,894,777 | 1/1990 | Negishi et al. . |
| 4,895,518 | 1/1990 | Arnold et al. . |
| 4,931,934 | 6/1990 | Snyder . |
| 4,978,303 | 12/1990 | Lampbell . |
| 4,983,125 | 1/1991 | Smith et al. . |
| 5,065,360 | 11/1991 | Kelly . |
| 5,079,726 | 1/1992 | Keller . |
| 5,170,362 | 12/1992 | Greenberg et al. . |
| 5,341,291 | 8/1994 | Roizeu et al. ...................... 364/413.02 |
| 5,344,324 | 9/1994 | O'Donnell et al. . |
| 5,392,030 | 2/1995 | Adams . |
| 5,410,305 | 4/1995 | Barrus et al. . |
| 5,511,982 | 4/1996 | Pigache et al. . |
| 5,529,498 | 6/1996 | Cassily et al. . |
| 5,551,880 | 9/1996 | Bonnstetter et al. . |
| 5,583,590 | 12/1996 | Clupper . |
| 5,595,488 | 1/1997 | Gozlan et al. . |
| 5,695,343 | 12/1997 | Jabourian . |
| 5,717,428 | 2/1998 | Barrus et al. . |

*Primary Examiner*—Max Hindenburg
*Assistant Examiner*—Brian Szmal
*Attorney, Agent, or Firm*—Crosby, Heafey, Roach & May; Adam H. Tachner; Leonard Tachner

[57] ABSTRACT

A special-purpose computer is provided along with a method for testing users for alertness and mental fitness before beginning work or a potentially dangerous activity. The system and method are usable wherever there is a risk to persons, property, or the environment from individuals not fit to operate machinery or enter an work area safely. The testing methods resemble computer games, but they actually measure mental fitness and alertness rather than aptitude, ability, or intelligence. The disclosed basic test is general, simple and non-intellectual, and compatible with worldwide, multilingual use. Other tests are more specifically designed to test for the ability to perform certain occupational duties or types of activities. The basic test preferably comprises a plurality of yes or no questions based upon graphical data displayed to the user. Each user's answers and performance are preferably maintained in strict confidence through storage only on a removable storage medium, such as a Smart Card.

24 Claims, 1 Drawing Sheet

ALERTNESS TESTER

CROSS-REFERENCE TO RELATED APPLICATIONS

This application claims priority from U.S. Provisional Patent Application Serial No. 60/042,577, entitled Alertness Testing System, filed Apr. 2, 1997, which is incorporated herein by reference. Also incorporated herein by reference is U.S. Provisional Patent Application Serial No. 60/058,841, entitled Brain Function Tester for All Ages, filed Sep. 15, 1997. Also incorporated herein by reference are the following disclosure documents filed with the U.S. Patent and Trademark Office: No. 394,198, entitled Special Purpose Computer System for Alertness and Readiness Testing, filed Mar. 4, 1996; No. 383,562, entitled Multilingual Software and its Use in Dedicated Computer System Used for Alertness and Readiness Testing, filed Mar. 11, 1996; No. 399,622, entitled Software and Hardware System to Test Alertness and Fitness, filed Jun. 6, 1996; No. 405,957, entitled Nonlinguistic Turnkey Test System for Mental Alertness and Awakeness, filed Oct. 16, 1996; No. 422,723, entitled Alertness Testing System with Alertness Gauge, filed Aug. 6, 1997; and No. 423,524, entitled Medical, Visual and Psychomotor Testing System, filed Aug. 21, 1997.

FIELD OF THE INVENTION

The present invention relates generally to the field of alertness testing, and more specifically to a system for implementing non-linguistic testing procedures for establishing and remotely recording a baseline level of alertness intended for comparison to a given test result.

BACKGROUND OF THE INVENTION

Accidents in the workplace cost many millions of dollars, hundreds of lives, and damage to the environment every year. The majority of these accidents are caused by human error. Human error has, of course, many causes, but it is most prevalent when an operator is impaired from lack of sleep, illness, or is under the influence of drugs or alcohol. In the U.S., 7.5 million workers in high-risk occupations are required to take random blood or urine tests to deter the use of drugs and alcohol on the job, a requirement which has helped reduce accidents. However, fatigue, illness and stress are more common causes of impairment than are the effects of drugs or alcohol. Accidents continue to occur in large part because workers are impaired by exhaustion, stress, side-effects from prescription medications or from a combination of these factors. There is therefore an urgent need for a way to screen workers for all impairment factors and causes before they begin work. Screening of this kind should be sensitive to impairment regardless of its cause, should be simple and quick, and should insure the maintenance of worker privacy.

SUMMARY OF THE INVENTION

The present invention addresses these concerns with a reliable and economical alertness tester which is easy to use and protects user privacy. The inventive tester preferably comprises a compact, single-purpose computer which can be hung on a wall, installed in a booth or mounted in an instrument panel. The inventive tester provides a standard for checking worker alertness which can be utilized throughout an industry or among entities nationally and internationally.

The present invention therefore comprises a system to assess a user's level of alertness or mental fitness by using computer-delivered tests and a personal data device (preferably a Smart Card, but referred to generally as a datacard). The datacard preferably permits or prevents the use of or access to equipment or work areas, depending on the person's level of alertness. The tester preferably maintains personal privacy by retaining test performance and baseline information only on each user's own datacard, which each user carries as personal property. Preferably, no personal data is retained in any computer, database or tester. Personal data are retained only on a user's own datacard, thereby maintaining user privacy. Each user's own personal level of test performance is coded into their own datacard. When a test ends, any performance data temporarily retained by the tester's memory is preferably automatically erased.

It is therefore an advantage of the present invention to provide a system and method for testing the alertness of a user, the system comprising, a microprocessor, a visual display apparatus in electrical communication with the microprocessor, a data I/O port in electrical communication with the microprocessor, a portable data storage device having a user data memory, the portable data storage device being releasably interfaceable with the data I/O port, thereby enabling data downloading to and data uploading from the microprocessor, a test memory in electrical communication with the microprocessor, the test memory being loaded with at least one executable software program comprising a user alertness test and a passing data set, the user alertness test comprising test information displayed on the visual display, an input mechanism in electrical communication with the microprocessor for receiving input data from the user in response to the test information displayed on the visual display, the microprocessor thereby being enabled to receive user data from the user data memory, receive the test data from the test memory, display the test information on the visual display, receive the input data from the user via the input mechanism, compare the input data to the passing data set, and assign either of a selected test performance-pass and a test performance-fail signal to the user depending upon the result of the comparison.

BRIEF DESCRIPTION OF THE DRAWINGS

The aforementioned advantages of the present invention, as well as additional advantages thereof, will be more fully understood hereinafter as a result of a detailed description of a preferred embodiment when taken in conjunction with the following drawing in which.

DETAILED DESCRIPTION OF A PREFERRED EMBODIMENT

Figure 1:
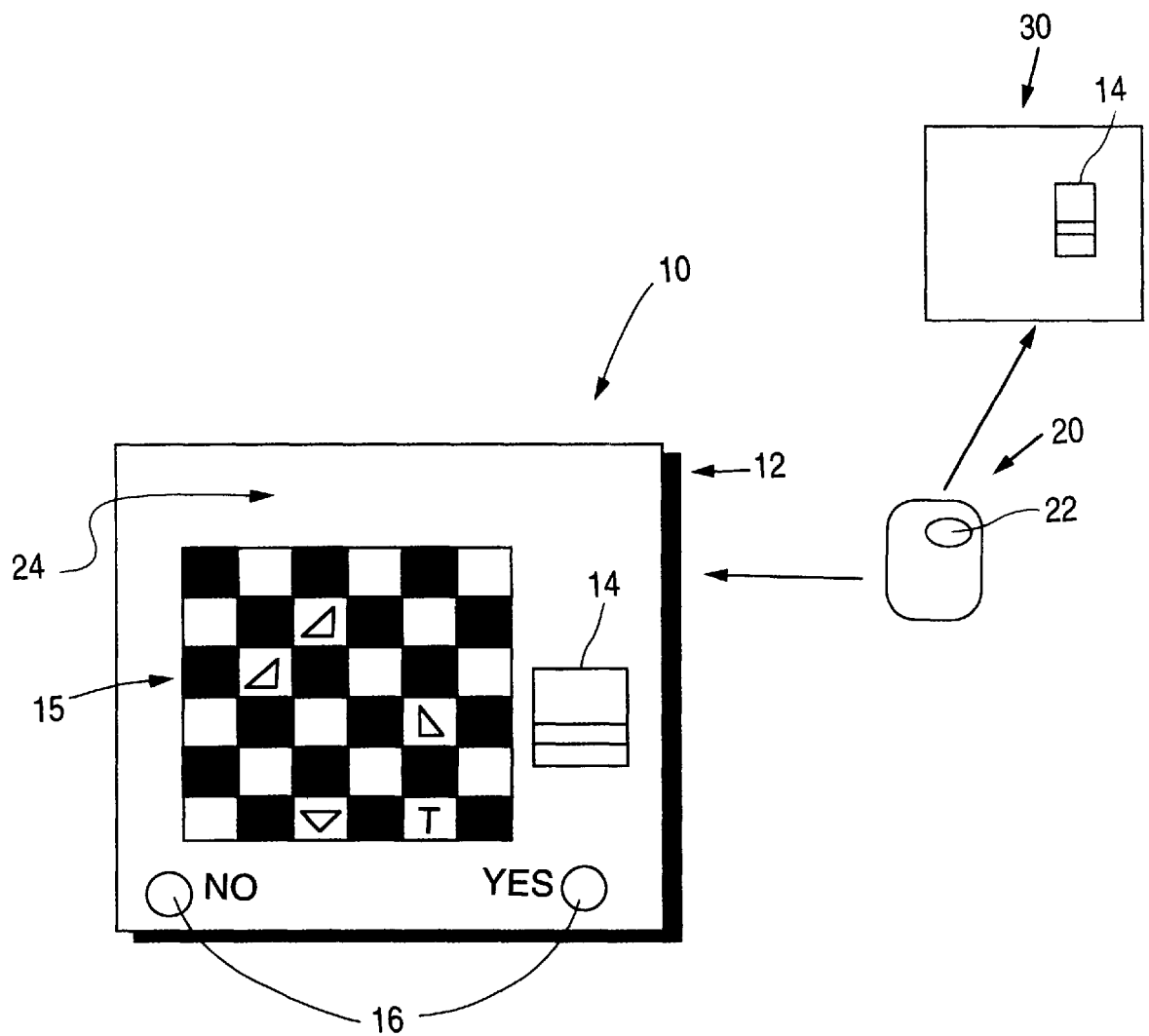
FIG. 1 illustrates a front view of the tester of the present invention.

Referring to FIG. 1, alertness tester 10 of the present invention comprises a computer, preferably, but not necessarily, a single-use device, which calculates a user's score on an alertness test and determines if the score is high enough to pass. A score must be at or near their baseline score to pass. If the user passes the test, then a pass code, plus the time and date, are written onto the user's ID card, referred to as a datacard 20.

A preferred test, implemented as software executable on the tester, preferably resembles a simple video game, and is completed quickly by a user (about one minute, preferably less). If a user performs particularly well on a given day, he or she preferably is provided an early exit and passing score after a shortened test period. A user's test result is preferably displayed on the screen before datacard 20 is removed, allowing the user to retake the test immediately if he or she failed. Also, an appropriate message is preferably displayed before testing begins if the user's datacard is invalid, unreadable, or otherwise not properly functioning. An error message or symbol may also be provided on the display. All game materials, indicators, and feedback are preferably displayed to the user in the form of nonlinguistic, graphic symbols. The visual display may also include an alertness gauge to graphically display the user's score relative to the user's baseline. The gauge may display the user's score relative to an absolute pass/fail line or relative to a range of passing or baseline scores, as per the system administrator's choice.

In a preferred test embodiment, the user decides whether a plurality of displayed figures (not shown) match by pressing YES or NO front panel buttons 16. Next to each button 16 is a write-on area where a supervisor or test administrator can erasably write "yes" and "no" in any language, as shown in FIG. 1 in English. NO and YES buttons 16 are preferably spaced far enough apart to allow users to use either one or both hands to respond. Also, the buttons are preferably large enough to be used while wearing gloves.

Enclosure 12 is preferably wall-mounted, and approximately one foot square and about three inches deep, deeper if a standard CRT is utilized. Datacard reader 14 is preferably accessible by the user from the front or side. An electric power connector is preferably located on one of the edges or on the rear surface, but preferably not on the front. The system may also be battery operated or rely on solar power or some alternative power source understood by one skilled in the art to which the present invention pertains. On front panel 24, there may also be a logo, company name, instructions and/or indicator lights.

The directions of primary data flow should be discussed to promote a better understanding of tester 10. First, user identity and, if available, baseline performance data is read when datacard 20 is first inserted into the tester. When a baseline is being established for a user, data is read from and written to the datacard. Once established, a baseline is preferably accessed at the start of each test and used for comparison to the user's test results. After testing, if the user passes the test, a pass code, date and time are written onto datacard 20 via datacard reader 14.

Each user is preferably equipped with a datacard, preferably a Smart Card, which stores the user's own predetermined baseline. A user's baseline is a measure of the user's normal daily level of alertness and mental fitness. If a user passes a test, a pass code is written onto their datacard, plus time and date. If a user fails a test, either a fail test code or no code is written onto the user's card.

Datacard 20 preferably comprises a Smart Card, also known as an Integrated Circuit Card (ICC) or a device where an integrated circuit 22 is contained within an identification card piece of plastic. A "memory button", a small memory integrated circuit having an I/O interface and worn or carried by the user may also be utilized. The preferred form factor for Smart Cards is 85.6 mm×53.98 mm×0.76 mm and is the same as the ubiquitous bank card with its magnetic stripe that is used as the payment instrument for numerous financial schemes. The datacard may have contacts or be contactless. A contactless card may contain its own battery, particularly in the case of a "Super Smart Card" which has an integrated keyboard and LCD display. In general however the operating power is supplied to the contactless card electronics by an inductive loop using low frequency electronic magnetic radiation. The communications signal may be transmitted in a similar way or can use capacitive coupling or even an optical connection. Most contact cards contain only a simple integrated circuit including a memory portion.

There are preferably at least two types of datacards, permanent and temporary. A pass code is written to a permanent datacard with a time and date stamp, and is erased when the card is used in an access control device. With a temporary datacard, the pass code fades away after a certain period of time, such as 5 minutes, as determined by the user's employer or other system administrator. While permanent datacards are less complicated (and therefore less expensive) than their temporary counterparts, the related access control device 30 is more complex since it must contain clocks and the ability to erase a pass code. Likewise, temporary datacards are more complex than permanent cards, but the necessary access control device need not contain clocks or erasing capabilities.

Datacards may also contain a visual indicator of a valid pass code. The least complex are nonindicating datacards, which provide no visual indication of having a valid pass code. A preferred embodiment of the present invention includes indicating datacards which have a visual indicator, such as a glowing or colored spot which indicates the presence or lack of a valid pass code in the datacard. Visual indices allow system administrators to utilize a security guard to check for access control, instead of an electromechanical access control device 30. This will be especially useful in some field operations where it is impractical to use a mechanized gate, turnstile or ignition cutoff. Datacards having visual indices are preferably of the temporary variety, described above, so that the visual indication of a pass code will expire in a short period of time, thereby deterring unauthorized use.

Permanently stored data on data cards preferably includes at least user name, identification number, company, security level, date of hire, testing level, and test type. All of this data is preferably stored only on the datacard, and accessed as needed by reader 14 during original baselining and rebaselining. During baselining, score data, date and time, are preferably retained on the datacards. Once a baseline is calculated, much of this data may be erased from the datacard. Therefore, some data memory registers in integrated circuit 22 are permanent, some temporary (those for baselining), and others, such as pass code, time and date, are erasable by access control device 30.

If a user passes a test, the user preferably removes the datacard from system 10 and moves to an access control switch 30. The access control switch must be opened in order to gain access to the device they will operate or to gain access into a secured area. The user preferably gains access only if he or she inserts datacard 20 into access control switch 30 within a time limit set by the system administrator (nominally 5 minutes or less). A clock (not shown) in an access control device is preferably set to UCT (Universal Coordinated Time) and determines whether each pass code is valid at the time of review (i.e., whether the pass code is used before expiration). Instead of using a clock in the access control device, the datacard may have a temporary location or storage medium (such as a capacitive switch), enabling the pass code to expire after a predetermined time.

Fundamental screening and baselining of users is preferably accomplished using a basic test to flag users who are significantly below their own normal daily level of alertness and mental fitness. After a group of users utilize the basic test for a predetermined period of time, the system administrator may obtain from the assignee of the present invention, or a licensed developer, a software upgrade. Upgrades may be aimed at testing for particular activity types, provide more stringent screening, or both. Software upgrades are preferably utilized simultaneous with previously installed software, thereby enabling each user to establish a new baseline for the upgrade without losing the use of the baseline established for the previously installed software. After a baseline is established for each user with the upgrade, the system administrator may decide whether users will take a plurality of tests in each test session, or if the previously installed test will be abandoned as soon as each user has a valid baseline for the new test. Another new test can then be introduced. Once a system administrator uses the basic test for a predetermined period of time, such as ninety days or more, other tests which are specific to certain types of jobs or impairments may be used.

The basic test preferably comprises a checkerboard pattern displayed on a display apparatus 15, as illustrated in FIG. 1. Other tests may be based on a board having other than an alternating background pattern, or no background pattern. A plurality of squares of alternating colors (e.g., black and white, as shown) are displayed as a background, while various figures, such as rectangles, triangles, or arrows, are displayed in the white squares in various orientations. The user's task is to press YES when all the shapes are the same, even if the various boxes include the same shape in a variety of orientations, and to otherwise press NO. Other tests may also include figures, or they may include other visual methodologies to test alertness. The inventive tester is intended for nonlinguistic use by people from any nation or linguistic origin. Thus, the screens preferably contain little or no language-based information. Preferably only nonlinguistic figures, graphics, or pictograms are used.

Normal functional levels of many aspects of psychomotor functions are preferably required from the user to pass the basic test, including visual perception, information processing, focused attention, decision-making, and eye-hand coordination. The basic test is useful for alertness testing because these psychomotor functions represent a person's general alertness and normal functioning and mental fitness. Thus, failing a test indicates that a user's alertness is reduced to a level below their own normal baseline, due to any cause.

A challenge is presented by those users who would purposely attempt to do poorly during the baselining process to enable them to reach a passing score on a later test, even when their alertness is impaired. To address this concern, the basic test preferably includes minimum performance standards applied to all users. Also, a new baselining period preferably begins for each user at the end of time period set by the system administrator, so that those users who would "cheat" the system will gradually move up in performance if they generally make an effort to pass the test on a regular basis.

The present invention therefore provides an inventive alertness testing apparatus including an adaptive baselining capability and a high level of confidentiality for users' performance and pass/fail information. The tester of the present invention is preferably used in conjunction with an access guarding device which regulates user-access to machinery or work spaces considered dangerous to operate when below a basic, subjective alertness level. The system may also be easily adapted for use as a performance-level tester, a brain function tester, an awakeness tester, a psycho-motor function tester, or a predictor of future alertness, awakeness, performance, or psycho-motor function. Indeed, the term "alertness" as used in the above description may be interchanged with these additional terms while still describing the form and function of the present invention. The inventive system may also be used as an assessor of medical fitness as described in provisional patent application serial No. 60/058,841 cited above. In the medical context, the access control device used in combination with the tester could be a medication dispenser, wherein the type and dosage of medication dispensed will depend on the user's score as recorded on the user's datacard or memory button. This description is therefore intended only to provide a preferred and alternative embodiments of the invention, which should be limited in scope only by the appended claims.

What is claimed is:

1. A system for testing the alertness of a user, the system comprising:

a microprocessor;

a visual display apparatus in electrical communication with said microprocessor;

a data I/O port in electrical communication with said microprocessor;

a portable data storage device having a user data memory, the portable data storage device releasably interfaceable with said data I/O port, thereby enabling data downloading to and data uploading from said microprocessor;

a test memory in electrical communication with said microprocessor, said test memory being loaded with at least one executable program comprising a user alertness test and a passing data set, the user alertness test comprising test information displayed on said visual display;

an input mechanism in electrical communication with said microprocessor for receiving input data from the user in response to said test information displayed on said visual display;

said microprocessor thereby being enabled to receive user data from said user data memory, receive said test data from said test memory, display said test information on said visual display, receive said input data from the user via said input mechanism, compare said input data to said passing data set, and assign either of a selected test performance-pass or a test performance-fail signal to said user depending upon the result of said comparison;

a remote access control means in electromechanical communication with either a machine, a work area or an item, for receiving said portable data storage device and either allowing the user to access or preventing the user from accessing the machine, work area or item based upon said test performance signal.

2. The system of claim 1, wherein said assignment of said selected signal is dependent upon a baseline level assigned to the user and received by said microprocessor from said portable data storage device.

3. The system of claim 1, wherein said input mechanism comprises a binary input signal selection apparatus.

4. The system of claim 1, wherein said alertness test comprises a set of questions and said passing data set comprises a set of answers to said set of questions.

5. The system of claim 4, wherein said set of questions is graphic-based.

6. The system of claim 1, wherein said input mechanism is integral with said visual display mechanism.

7. The system of claim 1, wherein said portable data storage device comprises either a smart card or a memory button.

8. The system of claim 1, wherein said selected signal is forwarded to said portable data storage device.

9. The system of claim 8 wherein said microprocessor forwards a datum indicative of the time or date to said portable data storage device with said selected signal.

10. The system of claim 8, wherein all information related to the user's performance on said alertness test is erased from said system after said selected signal is selected.

11. The system of claim 1, wherein all information related to the user's performance on said alertness test is erased from said system after said selected signal is selected.

12. A method for testing the alertness of a user with a system comprising a microprocessor; a visual display apparatus in electrical communication with the microprocessor, providing a data I/O port in electrical communication with the microprocessor; a portable data storage device having a user data memory, the portable data storage device being releasably interfaceable with the data I/O port, thereby enabling data downloading to and data uploading from the microprocessor; a test memory in electrical communication with microprocessor, the test memory being loaded with at least one executable software program comprising a user alertness test and a passing data set, the user alertness test comprising test information displayed on the visual display, and an input mechanism in electrical communication with the microprocessor for receiving input data from the user in response to the test information displayed on the visual display, the method comprising the steps of:

said microprocessor receiving user data from said user data memory;

said microprocessor receiving said test data from said test memory;

said microprocessor displaying said test information on said visual display;

said microprocessor receiving said input data from the user via said input mechanism;

said microprocessor comparing said input data to said passing data set, and assigning either of a selected test performance-pass or a test performance-fail signal to said user depending upon the result of said comparison;

an access control means in electromechanical communication with either a machine, a work area, or an item, for receiving said portable data storage device and either allowing the user to access or preventing the user from accessing the machine, work area or item based upon said test performance signal.

13. The method of claim 12, wherein said assignment of said selected signal is dependent upon a baseline level assigned to the user and received by said microprocessor from said portable data storage device.

14. The method of claim 12, wherein said input mechanism comprises a binary input signal selection apparatus.

15. The method of claim 12, wherein said alertness test comprises a set of questions and said passing data set comprises a set of answers to said set of questions.

16. The method of claim 15, wherein said set of questions is graphic-based.

17. The method of claim 12, wherein said input mechanism is integral with said visual display mechanism.

18. The method of claim 12, wherein said portable data storage device comprises either a smart card or memory button.

19. The method of claim 12, wherein said selected signal is forwarded to said portable data storage device.

20. The method of claim 19, wherein said microprocessor forwards a datum indicative of the time or date to said portable data storage device with said selected signal.

21. The method of claim 19, wherein all information related to the user's performance on said alertness test is erased from said system after said selected signal is selected.

22. The method of claim 12, wherein all information related to the user's performance on said alertness test is erased from said system after said selected signal is selected.

23. A system for testing the alertness of a user, the system comprising:

a microprocessor;

a visual display apparatus in electrical communication with said microprocessor;

a data I/O port in electrical communication with said microprocessor;

a portable data storage device having a user data memory, the portable data storage device releasably interfaceable with said data I/O port, thereby enabling data downloading to and data uploading from said microprocessor;

a test memory in electrical communication with said microprocessor, said test memory being loaded with at least one executable program comprising a user alertness test and a passing data set, the user alertness test comprising test information displayed on said visual display;

an input mechanism in electrical communication with said microprocessor for receiving input data from the user in response to said test information displayed on said visual display;

said microprocessor thereby being enabled to receive user data from said user data memory, receive said test data from said test memory, display said test information on said visual display, receive said input data from the user via said input mechanism, compare said input data to said passing data set, and assign either of a selected test performance-pass or a test performance-fail signal to said user depending upon the result of said comparison;

wherein said portable data storage device provides a temporary visual indicia of said performance-pass or performance-fail signal.

24. A system for testing the alertness of a user, the system comprising:

a microprocessor;

a visual display apparatus in electrical communication with said microprocessor;

a data I/O port in electrical communication with said microprocessor;

a portable data storage device having a user data memory, the portable data storage device releasably interfaceable with said data I/O port, thereby enabling data downloading to and data uploading from said microprocessor;

a test memory in electrical communication with said microprocessor, said test memory being loaded with at least one executable program comprising a user alertness test and a passing data set, the user alertness test comprising test information displayed on said visual display;

an input mechanism in electrical communication with said microprocessor for receiving input data from the user in response to said test information displayed on said visual display;

said microprocessor thereby being enabled to receive user data from said user data memory, receive said test data from said test memory, display said test information on said visual display, receive said input data from the user via said input mechanism, compare said input data to said passing data set, and assign either of a selected test performance-pass or a test performance-fail signal to said user depending upon the result of said comparison;

an access control means, for analyzing said portable data storage device and either allowing the user to access or preventing the user from accessing a desired destination or device, wherein said portable data storage device provides a temporary visual indicia.

* * * * *